(12) United States Patent
Chen

(10) Patent No.: US 6,946,174 B1
(45) Date of Patent: Sep. 20, 2005

(54) MOISTURE CURABLE BALLOON MATERIALS

(75) Inventor: John Jianhua Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 533 days.

(21) Appl. No.: 09/689,139

(22) Filed: Oct. 12, 2000

(51) Int. Cl.$^7$ .............................................. A61M 25/00
(52) U.S. Cl. ............................. 428/35.7; 604/171.23; 604/264; 604/280
(58) Field of Search .............................. 428/35.7, 34.9, 428/35.1, 36.8, 36.9, 36.92; 604/171.23, 264, 280

(56) References Cited

U.S. PATENT DOCUMENTS

| | | | |
|---|---|---|---|
| 4,146,585 A | 3/1979 | Ward et al. ................... 260/827 |
| 4,198,983 A | 4/1980 | Becker et al. ........... 128/349 R |
| 4,430,486 A | 2/1984 | Chang et al. .................... 525/44 |
| 4,490,421 A | 12/1984 | Levy ............................. 428/35 |
| 4,567,107 A | 1/1986 | Rizk et al. ................. 428/425.5 |
| 4,604,412 A | 8/1986 | Joh et al. ....................... 523/112 |
| 4,637,640 A | 1/1987 | Fournier et al. ............. 285/319 |
| 4,647,630 A | 3/1987 | Schmid et al. ............... 525/431 |
| 4,675,367 A | 6/1987 | Policastro et al. ........... 525/474 |
| 4,927,413 A | 5/1990 | Hess ............................ 604/95 |
| 4,988,778 A | 1/1991 | Chang et al. ............... 525/476 |
| 5,055,249 A | 10/1991 | Schmid ....................... 264/236 |
| 5,155,233 A | 10/1992 | Su et al. ...................... 549/202 |
| 5,227,434 A | 7/1993 | Katz ........................... 525/419 |
| 5,266,627 A | 11/1993 | Meverden et al. ........... 524/527 |
| 5,312,861 A | 5/1994 | Meverden et al. ........... 524/521 |
| 5,348,538 A | 9/1994 | Wang et al. .................... 604/96 |
| 5,439,443 A | 8/1995 | Miyata et al. ................. 604/96 |
| 5,599,352 A | 2/1997 | Dinh et al. ...................... 623/1 |
| 5,607,475 A | 3/1997 | Cahalan et al. ............... 623/11 |
| 5,702,754 A | 12/1997 | Zhong ....................... 427/2.12 |
| 5,702,818 A | 12/1997 | Cahalan et al. ............. 428/409 |
| 5,714,110 A | 2/1998 | Wang et al. ................. 264/529 |
| 5,735,830 A * | 4/1998 | Fritz et al. ................... 604/523 |
| 5,736,251 A | 4/1998 | Pinchuk ....................... 428/447 |
| 5,760,155 A | 6/1998 | Mowrer et al. ............... 528/28 |
| 5,762,996 A | 6/1998 | Lucas et al. .................. 427/2.3 |
| 5,782,908 A | 7/1998 | Cahalan et al. ................. 623/1 |
| 5,948,419 A | 9/1999 | Bankert et al. ............. 424/401 |
| RE36,330 E | 10/1999 | Ritscher et al. ............. 502/313 |
| 5,993,415 A | 11/1999 | O'Neil et al. ................. 604/96 |
| 5,998,551 A | 12/1999 | O'Neil et al. ............... 525/426 |
| 6,015,920 A | 1/2000 | Schilling et al. ............ 556/479 |
| 6,048,935 A | 4/2000 | Penfold et al. ............. 525/106 |
| 6,077,902 A | 6/2000 | Roesler et al. ............. 524/589 |
| 6,218,016 B1 * | 4/2001 | Tedeschi et al. .......... 428/423.1 |
| 6,329,488 B1 * | 12/2001 | Terry et al. .................... 528/28 |
| 6,479,584 B1 * | 11/2002 | Nakagawa et al. .......... 525/100 |

FOREIGN PATENT DOCUMENTS

| | | |
|---|---|---|
| EP | 0 651 005 A | 5/1995 |
| EP | 0 747 070 A2 | 12/1996 |
| GB | 2115699 A * | 9/1983 |
| WO | 96/23531 | 8/1996 |

* cited by examiner

*Primary Examiner*—Sandra Nolan Rayford
(74) *Attorney, Agent, or Firm*—Vidas, Arrett & Steinkraus

(57) ABSTRACT

The present invention relates to a catheter device having a dilatation balloon formed from a polymeric material crosslinked by moisture through —Si—O—Si—linkages, and to a method of making the same. The polymeric material is formed by reacting at least one organofunctional hydrolyzable silane with at least one polymer. The crosslinked polymeric structure is ideal for forming more resilient and durable catheter balloons. In particular, the catheter balloons have excellent abrasion resistance.

23 Claims, 1 Drawing Sheet

MOISTURE CURABLE BALLOON MATERIALS

FIELD OF THE INVENTION

The present invention relates to the preparation of thin films useful in medical devices, and in particular in the manufacture of medical dilatation balloons, formed from a durable polymeric composition crosslinked upon exposure to moisture through —Si—O—Si—linkages. More particularly, the balloons are formed from the reaction product of at least one organofunctional hydrolyzable silane and at least one polymer, the reaction product of which is crosslinked by exposure to moisture. The crosslinked structure increases the toughness, abrasion resistance, durability and dimension stability of the material during both manufacturing procedures and during use.

BACKGROUND OF THE INVENTION

Balloon catheters are used in procedures relating to the treatment of stenoses or blockages in body vessels, an example of which is an arterial stenosis which is commonly treated by angioplasty procedures which involve the insertion of balloon catheters into the affected blood vessel of the patient.

The balloon may finction to widen a vessel into which the catheter is inserted, to force open a blocked vessel to open the blocked or collapsed blood vessel, or to prop open the a collapsed vessel. The requirements for strength and size of the balloons vary widely depending on the balloon's intended use and the vessel size into which the catheter is inserted. Perhaps the most demanding applications for such balloons are in balloon angioplasty in which catheters are inserted for long distances into extremely small vessels and used to open stenoses of blood vessels by balloon inflation.

Balloon angioplasty requires extremely thin walled, high strength (i.e. high tensile) latively nelastic balloons of predictable inflation properties.

Thin walls are necessary because the balloon's wall and waist thicknesses limit the minimum diameter of the distal end of the catheter and therefore determine the limits on vessel size treatable by the method and the ease of passage of the catheter through the vascular system. High strength is necessary because the balloon is used to push open a stenosis and so the thin wall must not burst under the high internal pressures necessary to accomplish this task. The balloon must have some elasticity so that the inflated diameter can be controlled, so as to allow the surgeon to vary the balloon's diameter as required to treat individual lesions, but that elasticity must be relatively low so that the diameter is easily controllable. Small variations in pressure must not cause wide variation in diameter.

To achieve the high strength, thin walled properties, catheter balloons are often made of biaxially oriented polyethylene terephthalate (PET) or a polyamide material such as nylon 12. These materials, however, tend to be less elastic, and have less resilience.

Balloon catheters may also be made of more elastic materials such as polyolefins or polyolefin copolymers, but typically, in order to achieve the high tensile strength, the balloon walls must be made thicker.

One difficulty experienced in the case of the high strength, thin walled materials, such as PET is that they can be punctured through abrasion or the like, even though they have a high tensile strength. Pin holes and ruptures can occur when such catheter balloons are used in contact with rough surfaces. Also, tiny flaws in the mold of such balloons can create weak spots, since the balloons are so thin-walled.

It is, however, typically impractical to increase the wall thickness of these biaxially oriented, non-resilient materials because they become too stiff, with high flexural moduli, with the result that such balloons do not collapse properly on deflation to facilitate easy withdrawal from the vascular system of a patient.

The balloons can be coated with a more abrasion resistant material, but coatings add a step during the manufacturing process, typically decrease flexibility, and also typically increase the wall thickness.

There remains a need for a balloon catheter which is thin walled, durable, abrasion and tear resistant thereby improving the resistance to pinhole formation, and is relatively flexible, yet inelastic to allow the balloons to expand outwardly to a predetermined diameter, and then cease further expansion at normal pressures, to avoid damage to the artery wall by overexpansion.

SUMMARY OF THE INVENTION

The present invention relates to a medical device such as a balloon catheter comprising a dilatation balloon wherein said balloon comprises a moisture cured polymeric material which is crosslinked through —Si—O—Si—linkages.

The present invention further relates to a catheter balloon comprising the reaction product of at least one polymer and at least one organofunctional hydrolyzable silane having an organofunctional group capable of readily reacting with the moieties on the polymer backbone. The silane is grafted onto the polymer backbone and the hydrolyzable groups of the silane are activated by moisture, crosslinking the structure through —Si—O—Si—linkages.

The present invention further relates to a medical device comprising a dilatation balloon formed from a crosslinked polymeric material, the crosslinked polymeric material comprises the reaction product of at least one polymer and at least one hydrolyzable silane having the following general structure:

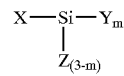

where X is a monovalent non-hydrolyzable organic moiety comprising at least one functional group W which is reactive with said polymer with the proviso that an Si—C bond is present between Si and W, Y is a hydrolyzable group, Z is a monovalent hydrocarbon group, and m is an integer from 1 to 3. The hydrolyzable silane groups, Y of the silane are then activated with moisture to form a durable, tough, high strength, excellent abrasion resistant polymeric material crosslinked through —Si—O—Si—linkages. The balloon structure also has dimension stability during both manufacturing procedures and in use. The high strength crosslinked material allows the balloons to be manufactured having of a relatively thin walled structure.

The present invention further relates to a method of forming a catheter balloon comprising the steps of providing at least one polymeric material at or above its melt temperature, providing at least one organofunctional hydrolyzable silane compound, extruding the polymeric material and the organofunctional hydrolyzable silane compound into a tubular preform at a temperature wherein the polymeric material and the hydrolyzable silane react, forming the tubular preform into a balloon preform, blowing the balloon preform into a balloon, and exposing the balloon or balloon preform to water. The hydrolyzable groups on the silane are activated by moisture forming a durable polymeric material crosslinked through —Si—O—Si—linkages..

Figure 1:
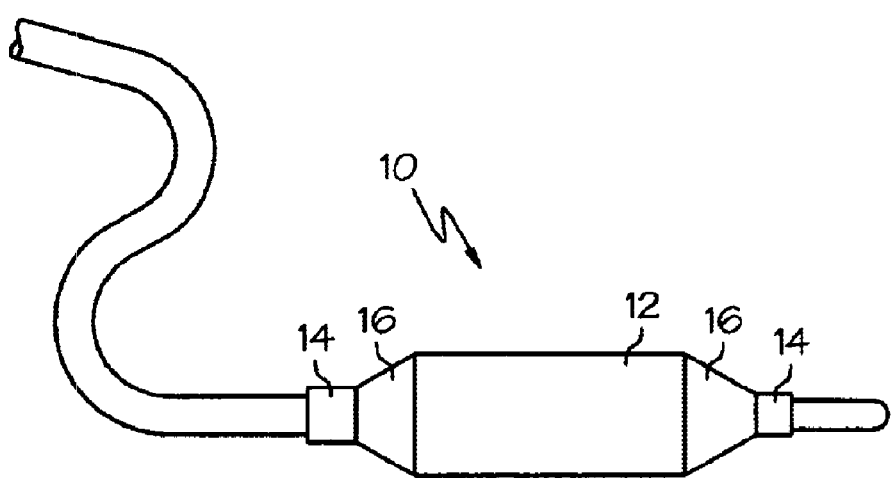
FIG. 1 is a perspective view of a dilatation catheter having attached at its distal end, a catheter balloon of the present invention depicted in its inflated state.

DETAILED DESCRIPTIONS OF THE
PREFERRED EMBODIMENTS

The present invention relates to medical balloons that are made of a durable polymeric material crosslinked through —Si—O—Si—linkages.

The method of preparing the medical balloons of the present invention involves the grafting of hydrolyzable silanes onto a polymer backbone and then moisture curing the resultant polymeric structure. The hydrolyzable groups of the silane are activated upon exposure to moisture forming durable —Si—O—Si—linkages.

The general reaction scheme representative of the grafting/moisture curing reaction of the present invention generally involves a two-step reaction process in which the first step is the reaction between the hydrolyzable silane compound and the polymer at melt in the absence of moisture, and the second step is the crosslinking reaction in which the hydrolyzable groups of the silane are activated with moisture forming the durable —Si—O—Si—linkages.

This two step process can be represented by the following general reaction scheme. The first step of the diagram illustrates the reaction between the polymer and the hydrolyzable silane compound. The second and third reactions illustrate hydrolysis and condensation of the polymer to form the —Si—O—Si—linkages. The latter two reactions occur basically simultaneously and are considered to be the second step.

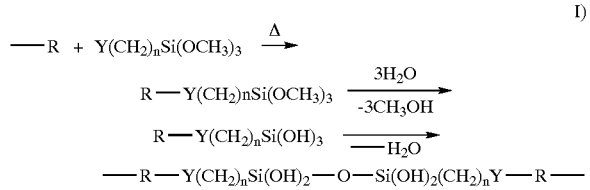

The silanes useful herein include those having hydrolyzable groups, each of which is bonded to the silicon atom and that will effectively graft and crosslink to a polymer backbone. Hydrolyzable groups include $C_1$ to $C_{12}$ alkoxy groups, in particular the lower $C_1$ to $C_4$ alkoxy groups such as methoxy or ethoxy, $C_2$ to $C_4$ acryloxy, up to about $C_6$ (poly)alkoxyalkoxy, phenoxy, oxime, amine, halogen groups including chlorine, fluorine and bromine, and so forth. In particular emodiments of the present invention, hydrolyzable groups including the alkoxy, alkoxyalkoxy and the acryloxy groups are used. The hydrolyzable groups, the alkoxy groups for instance, will be activated by moisture to form durable structures crosslinked through —Si—O—Si— linkages.

The organofinctional hydrolyzable silanes useful herein may be broadly represented by the following general structure:

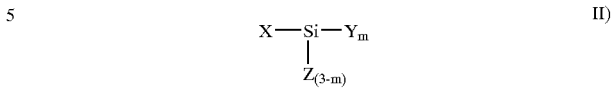

where X is a monovalent non-hydrolyzable organic moiety comprising at least one functional group W which is reactive with the polymeric material to which the silane is to be grafted with the proviso that at least one Si—C bond is present between Si and W, Y is a hydrolyzable group, Z is a monovalent hydrocarbon group, and m is an integer from 1 to 3. The hydrolyzable silane is useful from about 0.05 wt-% to about 20 wt-% of the polymer/silane composition. W may be, but is not limited to, (meth)acrylamido, (meth) acryloxy, carboxyl, epoxy, amino, ureido, isocyanato, thiocyanato, mercapto, haloalkyl, styryl, vinyl, allyl, sulfonyl azide, acid anhydride, or carboxylic acid esters of aromatic alcohols, the alcohols of which have 2 to 15 carbon atoms, and mixtures thereof.

In particular embodiments X is epoxycylohexyl, glycidoxypropyl, isocyanatopropyl, vinyl or allyl. Other examples of X include, but are not limited to, 3-acryloxypropyl, 3-methacryloxypropyl, 3-glycidoxypropyl, 2-(3,4-epoxycyclohexyl)ethyl, 3-aminopropyl, N-(2-aminoethyl)-3-aminopropyl, (aminoethylaminomethyl)phenethyl, 3-(1-aminopropoxy)-3,3-dimethyl-1-propenyl, N-phenylaminopropyl, diethylenetriaminopropyl, and 3-ureidopropyl. Organofunctional moieties containing amino functional groups or isocyanato functional groups are particularly versatile in having reactivity or compatibility with a wide range of different polymer types.

In particular embodiments, Y is $C_1$ to $C_4$ alkoxy, and m is 2 or 3.

Some examples of specific unsaturated silanes represented by formula II) above that are useful herein include, but are not limited to, those that comprise an ethylenically unsaturated hydrocarbyl group, such as a vinyl, allyl, isopropenyl, butenyl, cyclohexenyl or γ-(meth) acryloxyalkyl group, and a hydrolyzable group, such as, for example, a hydrocarbyloxy, hydrocarbonyloxy, or hydrocarbylarnino group. Examples of hydrolyzable groups include methoxy, ethoxy, formyloxy, acetoxy, proprionyloxy, and alkyl or arylamino groups.

Preferred silanes of this category are the unsaturated alkoxy silanes which can be grafted onto the polymer.

Some of these unsaturated silanes and their method of preparation are more fully described in U.S. Pat. No. 5,312,861 and U.S. Pat. No. 5,266,627, both of which are incorporated by reference herein in their entirety. Specific examples of these silanes for use herein are vinyl trimethoxy silane, vinyl triethoxy silane, γ-(meth)acryloxy propyl trimethoxy silane, allyltrimethoxysilane, and so forth.

A particular class of hydrolyzable silanes useful herein include those represented by the following general formula:

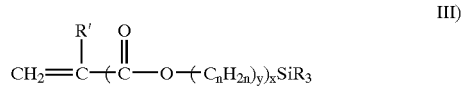

where R' is a hydrogen atom or lower $C_1$ to $C_4$ alkyl, particularly methyl; x and y are 0 or 1 with the proviso that when x is 1, y is 1; n is an integer from 1 to 12 inclusive, preferably 1 to 4, and each R independently is a hydrolyzable organic group such as an alkoxy group having from 1 to 12 carbon atoms (e.g. methoxy, ethoxy, butoxy), aryloxy group (e.g. phenoxy), araloxy group (e.g. benzyloxy), aliphatic acyloxy group having from 1 to 12 carbon atoms (e.g. formyloxy, acetyloxy, propanoyloxy), amino or substituted amino groups (alkylamino, arylamino), or a lower alkyl group having 1 to 6 carbon atoms inclusive, with the proviso that not more than one of the three R groups is an alkyl.

Other silanes useful herein include but are not limited to, 3-acryloxypropyltrimethoxysilane, 3-methacryloxypropyltimethoxysilane, 3-methacryloxypropyltris(methoxyethoxy)silane, 3-glycidoxypropyltrimethoxysilane, (3-glycidoxypropyl)methyldiethoxysilane, 3-aminopropyltriethoxysilane, 2-(3,4-epoxycyclohexyl)ethyltrimethoxysilane, (3-aminopropyl)methyldiethoxysilane, N-(2-aminoethyl)-3-aminopropyltrimethoxysilane, N-(2-aminoethyl)-3-aminopropylmethyldimethoxysilane, (aminoethylaminomethyl)phenethyltrimethoxysilane, 3-(1-amninopropoxy)-3,3-dimethyl-1-propenyltrimethoxysilane, N-phenylaminopropyltrimethoxysilane, (3-trimethoxysilylpropyl)diethylenetriamine, ureidopropyltriethoxysilane, 3-isocyanatopropyltriethoxysilane, 3-thiocyanatopropyltriethoxysilane, 3-mercaptopropyltriethoxysilane, 3-(N-styrylmethyl-2-aminoethylarnino)propyltrimethoxysilane hydrochloride, phenyltriethoxysilane, phenethyltrimethoxysilane, (p-chloromethyl)phenyltrimethoxysilane, (chloromethyl)phenylethyltrimethoxysilane, and so forth.

Suitable polymers include, but are not limited to, polyolefins such as polyethylene and polypropylene, and substantially linear ethylene and propylene α- olefins; acrylic polymers; copolymers of olefins and acrylic acid ester copolymers thermoplastic or elastomeric polyurethanes; thermoplastic or elastomeric polyesters; polyamides; polysulfones; polyvinyls; and so forth.

The incorporation of silanes into polyamides, as well as other polymers including polyolefins, is discussed in U.S. Pat. No. 4,637,640 and in U.S. Pat. No. 5,055,249 both of which are incorporated by reference herein in their entirety.

Some specific embodiments of the present invention are represented by the following reaction mechanisms. In some specific embodiments, an amino functional polymer, is reacted with an isocyanate functional hydrolyzable silane. Poly(meth)acrylate polymers having pendant hydroxy groups thereon can be also be reacted with isocyanato finctional alkoxysilanes. These types of reactions have been found to have particular utility herein.

For instance, an example of a reaction between the isocyanate functional silane compound, isocyanatopropyltriethoxy silane, and an amine containing polymer may be represented by the following general reaction scheme:

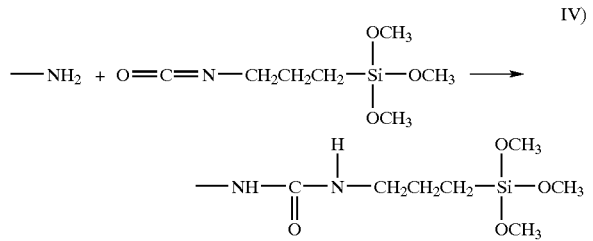

IV)

An example of a reaction in which a silane compound having epoxy functionality is reacted with a polymer having amine functionality may be represented by the following general reaction scheme:

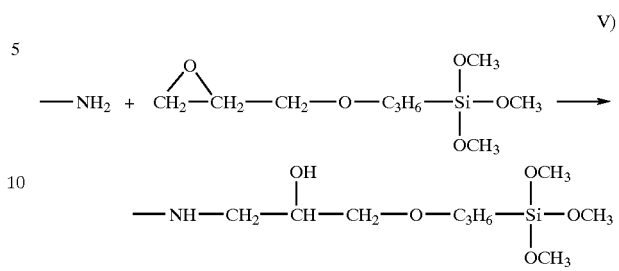

V)

Another example of a reaction between a different epoxy functional silane and a polymeric amine containing compound may be represented by the following general reaction scheme:

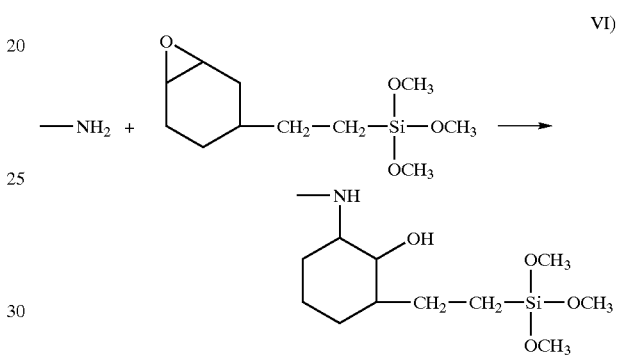

VI)

A specific method of grafting an unsaturated hydrolyzable silane onto the backbone of a polymer is by a free radical mechanism in which a free radical initiator, such as an organic peroxide, is used.

The following reaction mechanism is representative of an unsaturated silane, i.e. in this case a vinyl containing silane, reacted onto a polymer backbone by a free radical mechanism using a peroxide as the free radical initiator.

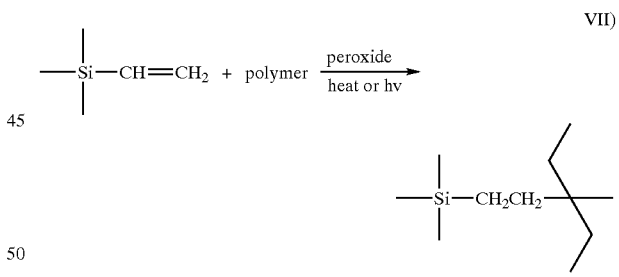

VII)

The second of the reaction process is a moisture curing step in which the hydrolyzable alkoxy groups of the silane in the presence of moisture, react to form polymers which are crosslinked by the presence of —Si—O—Si—linkages. These crosslinked polymers provide structures which are more durable, abrasion resistant, tear resistant and dimensionally stable during sterilization than non-crosslinked polymeric materials.

The resultant crosslinked material finds particular utility in medical devices, especially in angioplasty catheter balloons where the durability and toughness are especially important.

In the preparation of the medical devices of the present invention, a tubular preform is first prepared by mild blending and extruding the amine containing polymeric material and the finctional silane compound together at a temperature of greater than the metling temperature of the polymer(s) in the absence of moisture. The tubular preform may be prepared using any extrusion techniques known in the art.

The tubular preform may then be fed into a balloon mold. The balloon is then exposed to moisture in some form in order to produce the crosslinked balloon structure of the present invention. This exposure to moisture may occur by actually forming the balloon in a water bath at temperatures and pressures typically used for balloon formation, or it may occur after balloon formation, for instance by placing the already formed balloon in a water bath with or without pressure.

Balloons are typically formed using a blow molding technique. However, balloon formation may be carried out in any conventional manner with conventional extrusion and blowing techniques, but basically there are three major steps in the process which include extruding the tubular preform, blow molding the balloon and annealing the balloon. The preform may be axially stretched and/or biaxially oriented before it is blown. General techniques for balloon formation are discussed in U.S. Pat. No. 4,490,421 to Levy and in U.S. Pat. No. 5,348,538 issued Sep. 20, 1994 to Wang et al. FIG. 1 is a perspective view of dilatation catheter shown in its inflated state having attached at its distal end a catheter balloon shown generally at 10. Catheter balloon 14 is formed of the crosslinked polymeric material of the present invention and is conventional in its structure having a body portion 12, cone portions 14 and waist portion 16. One of skill in the art will recognize that th moisture cured polymeric materials of the present invention may be utilized in any catheter balloon configuration capable of being formed from a polymeric material, and that numerous modifications can be made to these structures without departing from the spirit and scope of the present invention.

The exposure of the alkoxy groups of the silane to moisture results in the crosslinking reaction. After forming, the balloon may be kept in the hot water bath under pressure and tension at conventional molding temperatures such as in the range of about 65° C. to about 145° C. for a predetermined time to ensure completion of the crosslinking process. Any remaining uncrosslinked functional groups, however, will undergo crosslinking over time.

The resultant process for manufacturing the improved balloons of the present invention is thus very simple without the introduction of extra steps into the process of preparing the tubular preform.

As compared to some prior art methods, there is no requirement for radiation or e-beams using the method of the present invention. One disadvantage known to using e-beams is that it is difficult to et a full cure without any chain scission occuring. Further, the e-beam process is not economical.

The embodiments described herein are in no way intended to limit the present invention and one of skill in the art will recognize that modifications can be made without departing from the spirit and scope of the present invention.

What is claimed is:

1. A medical device formed of moisture curable materials, comprising: a dilatation balloon formed from a crosslinked polymeric material, the crosslinked polymeric material comprising the reaction product of:
   I) at least one polymer; and
   II) at least one hydrolyzable silane having the following general structure:

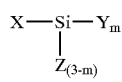

where X is a monovalent non-hydrolyzable organic moiety comprising at least one functional group W which is reactive with said polymer with the proviso that an Si—C bond is present between Si and W, Y is a hydrolyzable group, Z is a monovalent hydrocarbon group, and m is an integer from 1 to 3;
   said reaction product having been further reacted with moisture to produce a polymeric material crosslinked through —Si—O—Si—linkages.

2. The device of claim 1 wherein Y is an alkoxy group having from 1 to 4 carbon atoms.

3. The device of claim 1 wherein W is selected from (meth)acrylamido, (meth)acryloxy, carboxyl, epoxy, amino, ureido, isocyanato, thiocyanato, mercapto, styryl, vinyl, allyl, haloalkyl, acid anhydride, sulfonyl azide, carboxylic acid esters of aromatic alcohols, and mixtures thereof.

4. The device of claim 1 wherein X is selected from epoxycyclohexyl, glycidoxypropyl, isocyanatopropyl, vinyl, and allyl.

5. The device of claim 1 wherein said at least one hydrolyzable silane comprises an organofunctional group capable of readily reacting with a primary or secondary amine and said at least one polymer is an amino functional polymer.

6. The catheter device of claim 1 wherin said hydrolyzable silane is selected from isocyanatoalkylalkoxysilanes, glycidoxyalkylalkoxysilanes and epoxycylcohexylalkylalkoxysilanes.

7. The device of claim 6 wherein said hydrolyzable silane is selected form isocyanatopropyltriethoxysilane, glycidoxypropyltrimethoxysilane and 2-(3,4-epoxycyclohexyl) ethyltrimethoxysilane.

8. The device of claim 1 wherein at least one hydrolyzable silane has the following general structure:

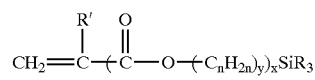

where R' is a hydrogen atom or lower $C_1$ to $C_4$ alkyl; x and y are 0 or 1 with the proviso that when x is 1, y is 1; n is an integer from 1 to 12 inclusive, preferably 1 to 4, and each R independently is a hydrolyzable organic group such as an alkoxy group having from 1 to 12 carbon atoms, aryloxy group, aralkoxy group, aliphatic acyloxy group having from 1 to 12 carbon atoms, amino or substituted amino groups, or a lower alkyl group havng 1 to 6 carbon atoms inclusive, with the proviso that not more than one of the three R groups is an alkyl.

9. The device of claim 8 wherein said reaction proceeds by a free radical mechanism.

10. The device of claim 1 wherein said free radical initiator is an organic peroxide.

11. The device of claim 8 wherein said hydrolyzable silane is selected from vinyltrimethoxysilane, vinyltriethoxysilane, allytrimetboxysilane, (-(meth) acryloxypropyltrimethoxysilane, and mixtures thereof.

12. A balloon catheter comprising a balloon wherein said balloon comprises a moisture cured polymeric material which is crosslinked through —Si—O—Si—linkages.

13. The balloon catheter of claim 12 wherein said moisture cured polymeric material is the reaction product of:
   a) at least one polymer; and
   b) at least one hydrolyzable silane having the following general structure:

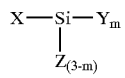

where X is a monovalent non-hydolyzable organic moiety comprising at least one functional group W which is reactive with said polymer with the proviso that an Si—C bond is present between Si and W, Y is a hydrolyzable group, Z is a monovalent hydrocarbon group, and m is an integer from 1 to 3.

14. The balloon catheter of claim 13 wherein said at least one hydrolyzable silane has an organofunctional group capable of readily reacting with a primary or secondary amine and said at least one polymer is amino functional.

15. The catheter balloon of claim 13 wherein Y is an alkoxy of $C_1$ to $C_4$.

16. The catheter balloon of claim 13 wherein W is selected from (meth)acrylamido, (meth)acryloxy, carboxyl, epoxy, aminio, ureido, isocyanato, thiocyanato, mercapto, styryl, vinyl, allyl, haloalkyl, acid anhydride, sulfonyl azide, carboxylic acid esters of aromatic alcohols, and mixtures thereof.

17. The catheter balloon of claim 13 wherein X is selected from epoxycyclohexyl, glycidoxypropyl, isocyanatopropyl, vinyl, and allyl.

18. The catheter balloon of claim 13 wherein said hydrolyzable silane is selected form isocyanatopropyltriethoxysilane, glycidoxypropyltrimethoxysilane and 2-(3,4-epoxycyclohexyl) ethyltrimetboxysilane.

19. The catheter balloon of claim 12 wherein said moisture cured polymeric material is the reaction product of:
   a) at least one polymer; and
   b) at least one hydrolyzable silane having the following general structure:

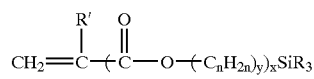

where R' a hydrogen atom or lower $C_1$ to $C_4$ alkyl; x and y are 0 or 1 with the proviso that when x is 1, y is 1; n is an integer from 1 to 12 inclusive, preferably 1 to 4, and each R independently is a hydrolyzable organic group such as an alkoxy group having from 1 to 12 carbon atoms (e.g. methoxy, ethoxy, butoxy), aryloxy group (e.g. phenoxy), araloxy group (e.g. benzyloxy), aliphatic acyloxy group having from 1 to 12 carbon atoms (e.g. formyloxy, acetyloxy, propanoyloxy), amino or substituted amino groups (alkylamino, arylamino), or a lower alkyl group having 1 to 6 carbon atoms inclusive, with the proviso that not more than one of the three R goups is an alkyl.

20. The medical device of claim 1 wherein said at least one polymer is a polyethylene, polypropylene or copolymers thereof, copolymers of ethylene and at least one ∀-olefin and propylene ∀-olefins.

21. The medical device of claim 1 wherein said crosslinked polymeric material is the reaction product of at least one amino functional polymer and at least one isocyanate functional hydrolyzable silane.

22. The medical device of claim 1 wherein said crosslinked polymeric material is the reaction product of at least one poly(meth)acrylate polymer having pendant hydroxy groups and at least one isocyanato functional alkoxysilane.

23. The device of claim 9 further comprising a free radical initiator.

* * * * *

UNITED STATES PATENT AND TRADEMARK OFFICE
CERTIFICATE OF CORRECTION

PATENT NO. : 6,946,174 B1 Page 1 of 1
DATED : September 20, 2005
INVENTOR(S) : John Chen It is certified that error appears in the above-identified patent and that said Letters Patent is hereby corrected as shown below:

Column 8,
Line 24, delete "catheter";

Column 9,
Lines 16, 18, 24, 27 and 32, delete "catheter balloon" and insert -- balloon catheter --.

Signed and Sealed this

Twenty-second Day of November, 2005

JON W. DUDAS
*Director of the United States Patent and Trademark Office*